United States Patent [19]
Becker

[11] Patent Number: 4,860,774
[45] Date of Patent: Aug. 29, 1989

[54] FINGERNAIL REINFORCEMENT MATERIAL AND METHOD

[75] Inventor: Mary G. Becker, Fort Lauderdale, Fla.

[73] Assignee: Maria Talerico, Ft. Lauderdale, Fla.; one half interest to each

[21] Appl. No.: 881,065

[22] Filed: Jul. 2, 1986

Related U.S. Application Data

[63] Continuation-in-part of Ser. No. 805,610, Dec. 6, 1985, abandoned, and Ser. No. 618,267, Jun. 7, 1984, abandoned.

[51] Int. Cl.$^4$ ............................................. A45D 40/30
[52] U.S. Cl. .................................... 132/200; 132/73; 427/340; 428/289; 428/442
[58] Field of Search .................. 132/88.5, 88.7, 73; 427/340; 428/289, 290, 442

[56] References Cited

U.S. PATENT DOCUMENTS

| | | | |
|---|---|---|---|
| 2,581,982 | 1/1952 | Terry | 132/73 |
| 2,864,384 | 12/1958 | Walter | 132/73 |
| 3,425,426 | 2/1969 | Welanetz | 132/73 |
| 3,552,401 | 1/1971 | Michaelson | 132/73 |
| 4,157,095 | 6/1979 | Sweet | 132/73 |
| 4,299,243 | 11/1981 | Umstattd | 132/73 |
| 4,455,342 | 6/1984 | Fink et al. | 428/290 |
| 4,536,426 | 8/1985 | Massey | 132/73 |
| 4,627,453 | 12/1986 | Isler | 132/73 |

OTHER PUBLICATIONS

Sagarin, Cosmetics, 1957, pp. 680-683.

Primary Examiner—Richard J. Apley
Assistant Examiner—Paul Prebilic
Attorney, Agent, or Firm—Malin, Haley & McHale

[57] ABSTRACT

There is disclosed herein a fingernail reinforcement extension material. The material is formed of a woven fiberglass fabric having a vertical and horizontal cross-thread count in the range of 25 to 55 threads per inch. Impregnated within said fabric is a preparation including cellulose, nylon fiber, resin, plasticizer and solvent in which, upon evaporation of the solvent, the preparation forms a hardened matrix within the weave of the fiberglass fabric.

Also disclosed is a method for the use of the material in order to accomplish the reinforcement and extension of human fingernails.

There is disclosed herein a fingernail covering for reinforcement of nails. The nail covering is formed of a woven fiberglass having a vertical and horizontal cross-thread count in the range of 25 to 55 threads per inch. Said fabric is preimpregnated with a suspension of resin polymer and monomer in water. The fabric is allowed to dry whereby the fabric is stabilized and the interstices between the threads are open. The fabric is coated with pressure sensitive adhesive.

Also disclosed is a method for the preparation of the nail covering and the application thereof to the nails.

25 Claims, 3 Drawing Sheets

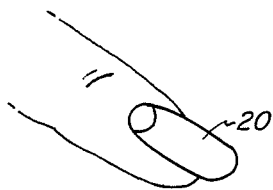
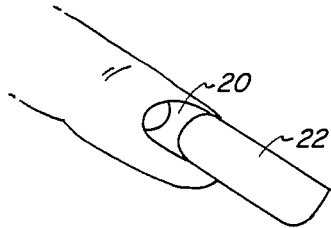
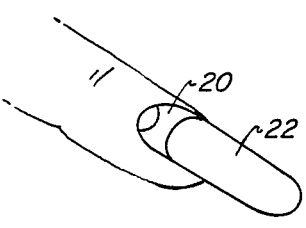
FIG. 11  FIG. 12  FIG. 13
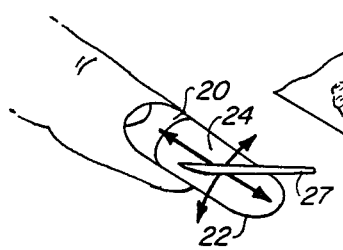
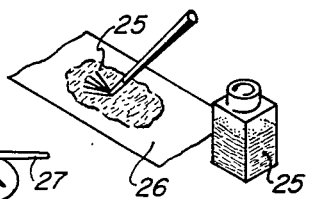
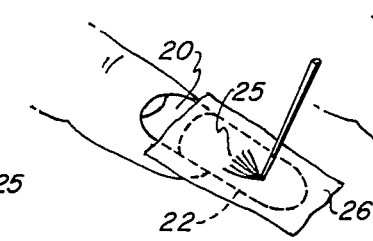
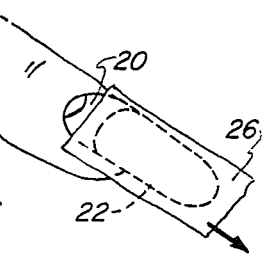
FIG. 14  FIG. 15  FIG. 16A  FIG. 16B
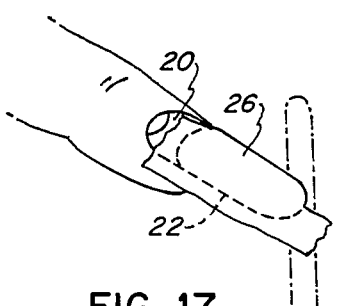
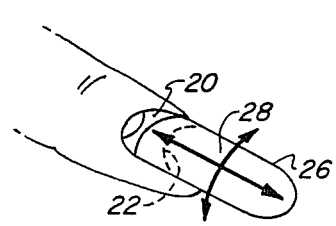
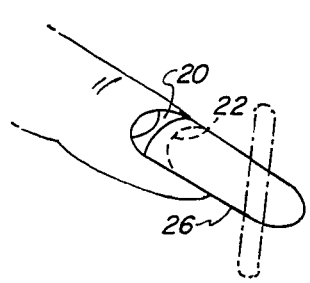
FIG. 17  FIG. 18  FIG. 19
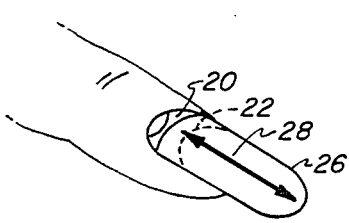
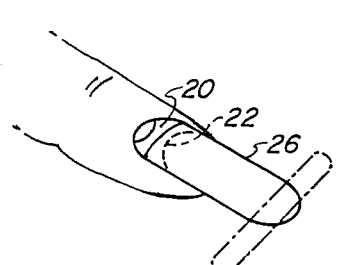
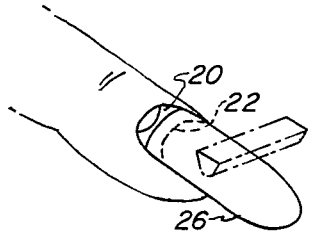
FIG. 20  FIG. 21  FIG. 22
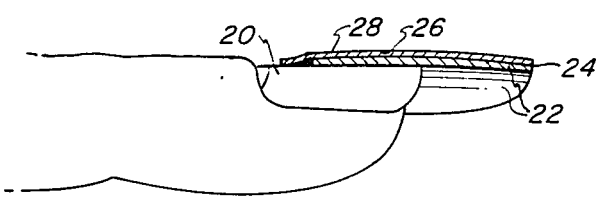
FIG. 23

FINGERNAIL REINFORCEMENT MATERIAL AND METHOD

REFERENCE TO RELATED APPLICATION

This is a continuation-in-part of application, Ser. No. 06/618,267, filed on June 7, 1984, and of Ser. No. 06/805,610 filed on Dec. 6, 1985 both now abandoned.

BACKGROUND OF THE INVENTION

1. Field of Invention

This invention relates to a cosmetic product and its preparation and application and, more particularly, to a fingernail covering.

The subject of this invention is believed to be in Class 132, Subclass 73.

2. Description of Prior Art

Long, carefully manicured fingernails are fashionable and enhance the overall feminine appearance. Long fingernails project beyond the tip of the finger or natural nailbed, often up to a distance of one-half inch or more, and are especially prone to cracking, chipping, breaking or splitting.

Many methods have been developed in an attempt to protect the extended end of the fingernail. These methods fall generally into three classes.

The first method consists of permanently or semi-permanently attaching a pre-formed artificial fingernail, herein referred to as "substrate", to the upper surface of the natural nail. The substrate is polished in a conventional manner from material that is less susceptible to wear and abrasion than is the natural nail.

The above method has several limitations. In particular, as the natural nail grows, a ridge forms at the back edge of the substrate. This ridge is not present when the back edge of the artificial nail or substrate abuts against the cuticle, but is exposed as the nail artificial nail or grows out. The ridge detracts from the smooth appearance of the nail, and can get caught on sharp objects resulting in the substrate splintering or peeling away from the artificial nail or natural nail. A second problem relates the difficulty in matching the size of the pre-formed nail or substrate with the natural nail. The artificial nail or substrate must completely cover the natural nail to avoid the presence of unsightly ridges. However, if the artificial nail or substrate extends beyond the side of the natural nail, extreme discomfort can result. Differences in natural nail curvatures complicate the application of the artificial nail or substrate.

The second general method consists of applying a coated material to the surface of the nail which hardens thereon and forms an artificial fingernail. The artificial nail thus formed is very similar, when dry, to the pre-formed substrate. However, it is sometimes difficult to apply the paint-on nail to fingernails of different shapes and sizes. The paint-on artificial nail is usually applied through a mask having a pre-formed artificial nail or cut-out. In this method, problems can occur when the cut-out is not the same size and shape as the natural nail. When operating properly, the mask is placed precisely about the nail bed and build-up material is applied to the nail bed. The mask protects the surrounding skin from irritation by exposure to the build-up material and acts as a support to form a free edge for an extended nail.

The third and most recent method relates to reinforcement of fingernails using a thin sheet of close weave porous reinforcing material covering outward portions of the nail. This third method comprises a plurality of steps in which the reinforcing material is impregnated during application to the nail, with a quick drying liquid adhesive, alternating with a plurality of shaping and smoothing steps. The reinforced portion of the fingernail forms a smooth, continuous surface with the non-reinforced portion of the fingernail.

The most pertinent prior art of which the Applicant is aware are U.S. Patent Nos. 2,581,982; 3,425,426; 3,478,756; 3,502,088; 4,157,095; and 4,299,243.

Patent No. 2,581,982 to Terry; No. 3,425,326 to Welanetz; and No. 4,299,243 to Umstattd, all disclose the impregnation of a woven fabric with either an adhesive or a solvent; however, none of said patents, or other prior art known to the Applicant, discloses the pre-impregnation of the fabric as claimed in this invention prior to its usage in the manicuring process. Also, the prior art discloses the use of woven fabrics limited to silk and cotton, both of which have close weaves. A problem with such closely-woven fabrics is that adhesive materials do not penetrate the fabric and therefore, do not provide sufficiently strong adhesion to the surface of fingernails. Also, silk lacks firmness and "body." Furthermore, both cotton and silk fingernail coverings fray when they are cut.

SUMMARY OF THE INVENTION

To overcome the above-mentioned problems, the fingernail covering of this invention comprises a woven fibreglass fabric having vertical and horizontal crossthread counts in the range from 25 to 55 threads per inch. The fibreglass cloth is stabilized by pre-impregnation with a suspension of a resin monomer and polymer in water, and evaporation of the water, whereby polymerization of the monomer causes the threads of the fabric to be bonded to each other. After the fabric has been thus stabilized, the interstices between the threads are open. One side of the stabilized fabric is then coated with a pressure-sensitive adhesive and pressed onto a rectangular sheet of wax paper backing with the fabric threads at a 45° angle with respect to the edges of the wax paper backing.

In application of the nail covering to the surface of fingernails, rectangular strips of the fingernail covering having the width and length of the fingernails to be covered are cut, with the cuts parallel to the edges of the wax paper backing. This insures that the fabric threads are cut at a 45° angle, a feature which avoids fraying along the cut edges.

The application of the nail covering to a fingernail surface comprises the steps of detaching a strip of fabric from its wax paper backing; pressing the side coated with the pressure sensitive adhesive onto the fingernail; and applying fast-drying adhesive onto the strip, whereby said fast-drying adhesive penetrates through the interstices of the fabric strip onto the fingernail surface. Upon drying of the fast-drying adhesive, a firm bond is formed between the fabric strip and the fingernail, whether it be natural nail or natural nail extended with substrate.

It is the object of this invention to provide a durable, non-fraying nail covering for reinforcement of fingernails.

It is another object of this invention to provide a simple and economical method for producing the nail covering.

It is a yet further object to provide a fingernail covering which firmly bonds to the fingernail surface due to its porosity.

It is to be noted that the nail covering is used for reinforcing a natural nail or a substrate which is applied to lengthen the existing fingernail. With the prolonged use of the nail covering of the present invention, the natural nail will grow to the desired length without recourse to a substrate such as an artificial nail to extend the nail length.

BRIEF DESCRIPTION OF THE DRAWINGS

FIG. 11 shows the natural fingernail.

FIGS. 12 and 13 show the optional step of utilizing a substrate or palate prior to beginning the present method.

FIG. 14 shows the step of applying a coat of slow-drying adhesive to a portion of the natural nail surface, and of contouring said adhesive.

FIG. 15 shows the step of applying a wetting solution to the impregnated fabric to provide flexibility thereto.

FIG. 16A shows the step of applying a piece of the wetted impregnated fabric over the molded adhesive, and FIG. 16B shows the step of tugging the tip of the impregnated fabric to effectuate the final contour thereof.

FIG. 17 shows the step of trimming the excess fabric on the sides of the natural nail to achieve a blending between the fabric and the natural nail.

FIG. 18 shows the step of applying, in vertical and horizontal directions, the fast-drying adhesive over the impregnated fabric.

FIG. 19 shows the step of feather filing the hardened adhesive to smooth all edges and surfaces thereof.

FIG. 20 shows the step of repeating the application of the fast-drying adhesive, shown in FIG. 8.

FIG. 21 shows the step of repeating the feather filing of FIG. 9.

FIG. 22 shows the step of buffing the hardened fast-drying adhesive to produce the final shape and lustre of the artificial nail.

FIG. 23 is a cross-section of a fingernail that has been treated in accordance with the present reinforcement and extension method of the invention.

DETAILED DESCRIPTION OF THE INVENTION

In accordance with the present invention, a fingernail covering is formed of woven fiberglass fabric having a vertical and horizontal crossthread count of from 25 to 55 threads per inch and weighing between 25 and 50 grams per square meter. The fiberglass fabric is preimpregnated with a suspension in water of a bonding material consisting primarily of polymers and monomers of acrylic resins. "Pre-impregnation" as used herein refers to impregnation of the fabric for the purpose of mechanical stabilization of threads of the fabric before its use in the manicuring process. For convenience, the word "fingernail" includes also toenail. The word "nails" refers to those of fingers and toes.

The preimpregnation suspension comprises acrylate and methacrylate ester monomer, their polymers or copolymers with vinyl acetate; other additives; and water. The preferred preimpregnation suspension comprises acrylic polymer in residual acrylic monomer, ethylene glycol and trace of ammonia (25 ppm). It is sold under the tradename "LAMIN-ALL" by McDonald Photo Products, Inc. This suspension is diluted 8–16 fold by volume with water. The extent of dilution depends on the closeness of the fiberglass threads to be impregnated. A more dilute suspension is used for closely woven fabric and a more concentrated suspension is used for more loosely woven fabric.

Pre-impregnation of the fiberglass may be carried out by brush or roller, but preferably by spraying. The fabric is initially saturated with the preimpreganting suspension as described above. The wet fabric is air dried without contact with any surface. The threads of the fabric are bonded to the dried suspension and the fabric is thereby stabilized. However, the interstices between the threads remain open, which provides porosity for penetration by adhesives used subsequently for application of the fabric to the fingernail.

On one side of the dried fabric, there is coated a layer of pressure-sensitive adhesive so as to provide a "self adhesive" backing. Many such adhesives are commercially available. A preferred adhesive is sold by 3M Company, under the tradename SUPER 77. The adhesive coated side of the fabric is then pressed against a rectangular wax paper backing with its threads at a 45° degree angle with respect to the edges of said wax paper backing. The finished sheet is then cut, parallel to its edge, into strips in widths and lengths according to the dimensions of the fingernails to be covered. It should be apparent that the threads of the fingernail covering thus prepared are at a 45° angle with respect to the axis of the strip length. The sheet may also be precut into different nail shapes. The fabric does not fray along the edges because of the stabilization of the fabric by preimpregnation and because the fabric threads are cut at a 45° angle.

Figure 1:
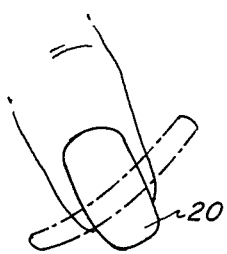
FIG. 1 shows the preparation of a fingernail by filing.
Figure 2:
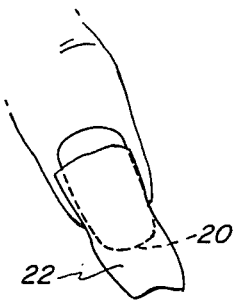
FIGS. 2 and 3 show the option step of utilizing a substrate to extend beyond the natural nail, prior to beginning the present method.
Figure 3:
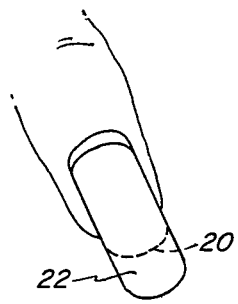

A process for reinforcing a fingernail in accordance with the present invention is illustrated in the drawings. FIG. 1 shows preparation of a natural fingernail 20 prior to reinforcement. FIGS. 2 and 3 show the optional steps of application to the natural nail of a substrate 22 which may be a plastic pre-formed nail, prior to commencement of the present inventive method. The application of substrate has long been known and had constituted the first step in every known nail extension method where greater length of the nail is an objective of a woman. The substrate is nothing more than a plastic base for all subsequent steps, whether in this or in any other nail extension method. As noted, the use of the substrate is optional and is necessary only where extension, as opposed to reinforcement or strengthening natural nails alone, is desired. As noted in FIG. 2, the substrate is first applied, by an adhesive such as cyanoacrylate, to the natural nail. As shown in FIG. 3, the substrate is shaped to the desired configuration and length.

Figure 4:
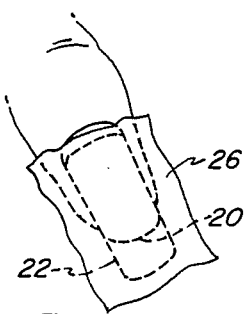
FIG. 4 shows the step of positioning of a strip of the nailcovering with threads of the fabric at a 45° angle with respect to the length of the nail.
Figure 5:
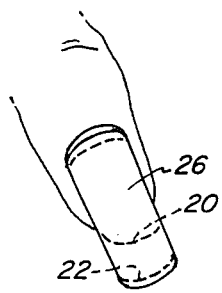
FIG. 5 shows the trimming of excess fingernail covering.
Figure 6:
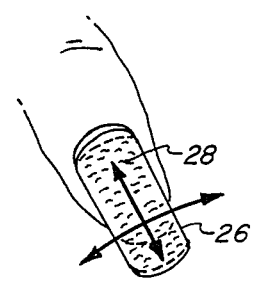
FIG. 6 shows application of fast-drying adhesive, in both longitudinal and transverse directions over the fingernail covering.
Figure 7:
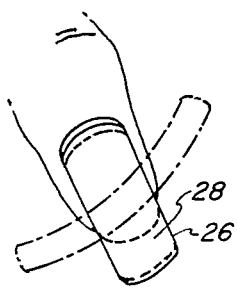
FIG. 7 shows feather filing the hardened adhesive to smooth all edges and surfaces thereof.
Figure 8:
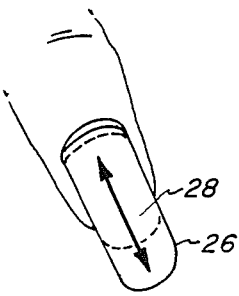
FIG. 8 shows repeating the application of adhesive as shown in FIG. 6.
Figure 9:
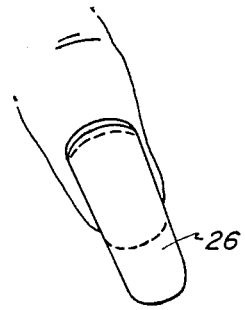
FIG. 9 shows in exaggeration, the layer of substrate covering a portion of the nail surface and the fingernail covering covering the substrate and the remaining uncovered nail and the adhesive covering all layers.
Figure 10:
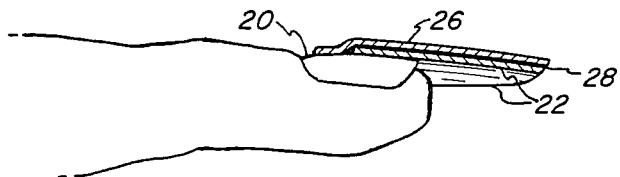
FIG. 10 is an axial cross-sectional side view of FIG. 9.

The present method of fingernail reinforcement is shown beginning in FIG. 4, illustrating the superimposition of a "self-adhesive" nail covering 26 in accordance with the present invention. FIG. 5 shows the step of trimming of excess fabric on the side and at the end to coincide with the underlying natural nail and the substrate. FIG. 6 shows the step of firmly pressing a coating of fast-drying cayanoacrylate adhesive 28, in both the longitudinal and transverse directions, thus sealing all the pores and edges, forming a solid smooth coating. This adhesive dries in approximately five seconds. FIG. 7 shows the feather filing of the hardened adhesive 28 in order to prepare the surface for the next step of coating with a second layer of adhesive. FIG. 8 shows the optional step of repeating the step of FIG. 6, as many times as desired, until the desired thickness of the nailcovering surface is achieved. FIG. 9 shows the finished reinforced nail, the underlying nail and substrate. FIG. 10 is a cross-sectional axial view of FIG. 9 indicating the substrate 22 over a portion of the natural nail 20, the nail covering 26 over the natural nail, and the adhesive 28 between nail covering 26 and substrate 22. To some extent, the adhesive 28 will also be left, as a film, on top of covering 26, per FIG. 7.

Where false nails (substrate 22) are not used, covering 26 and adhesive 28 will of course rest on the natural nail 20.

The present invention relates generally to the maintenance of fingernails and, more specifically, to both a new material particularly adapted for reinforcement and extension of the fingernails, and to a particular method for the use of such inventive reinforcement and extension material.

The most relevant area of classification is believed to comprise U.S. Class 132, Sub-class 73.

The original application set forth the following summary of the invention.

The instant invention relates to a fingernail reinforcement and extension material, the material comprising a woven fiberglass fabric having a vertical and horizontal cross-thread count in the range of 25 to 55 threads per inch; and a preparation pre-impregnated within the weave of said fabric, said preparation consisting essentially of cellulose, nylon fiber, resin, plasticizer and a solvent, whereby upon evaporation of said solvent, said preparation will form a hardened matrix within the weave of said fiberglass fabric, thereby forming a useful fingernail reinforcement and extension material.

It is an object of the present invention to provide a novel material and method for the reinforcement and extension of fingernails.

It is another object of the present invention to provide a simple step-by-step procedure for the reinforcing and extension of fingernails.

It is a yet further object to provide a material and method for the extension and reinforcement of fingernails that will enjoy enhanced life, durability, comfort and safety versus artificial fingernails known in the prior art.

The above and yet further objects and advantages of the present invention will become apparent from the hereinafter set forth Detailed Description of the Invention, the Drawings and Claims appended herewith.

The original application set forth the following detailed description of the invention.

With reference, firstly, to the inventive fingernail reinforcement and extension material, this inventive material is formed through the use of a woven fiberglass fabric having a vertical and horizontal cross-thread count in the range of 25 to 55 threads per inch. This fiberglass fabric is then impregnated with a preparation consisting essentially of cellulose, nylon fiber, resin, a plasticizer, and a solvent, whereby, upon evaporation of the solvent, the preparation forms a hardened matrix in the weave of the fiberglass fabric.

The following example has been found to satisfactorily include the necessary cellulose, nylon fiber, resin, plasticizer and solvent to define the preferred embodiment of the invention:

| EXAMPLE | |
|---|---|
| Ingredient | Quantity in grams |
| Nitrocellulose (½ second viscosity) | 121 |
| Nitrocellulose (20–30 second viscosity) | 10 |
| Ethyl cellulose | 15 |
| Gum Camphor | 20 |
| Toluene sulfonamideformaldehyde | 39 |
| Dihydromethyl abietate resin | 10 |
| Dibutyl phthalate | 15 |
| Sodium lauryl sulfate | 7 |
| Butyl acetate | 190 |
| Ethyl acetate | 140 |
| Ethyl alcohol | 140 |
| Monoethyl ether of ethylene glycol | 80 |
| Toluene | 57 |

The butyl acetate, ethyl acetate, ethyl alcohol, monoethyl ether of ethylene glycol, and toluene are all solvents and, it is to be appreciated, numerous variants thereof would be suitable in forming the present fingernail reinforcement and extension material. Generically, the usable solvents are believed to be properly selected from the group consisting essentially of alkyl alcohol, alkyl acetate, the alkyl group containing from one carbon to five carbons, acetone, methyl ethyl ketone, and any organic solvent.

The generic expression of the cellulose suitable for use in the impregnating preparation comprises a group consisting essentially of nitrocellulose and cellulose acetate.

The preferred resin is toluene sulfonamideformaldehyde.

Plasticizers suitable for use in the impregnating preparation may, generically, be selected from the group consisting essentially of di-alkyl phthalates, alkyl stearates, camphor, castor oil, coconut oil or any combination thereof. The di-alkyl phthalate may comprise dibutyl and diethyl phthalates.

In the below set forth method of usage of the above fingernail reinforcement and extension material, the use of a wetting agent is necessary. This wetting agent may comprise any solvent selected from the group consisting essentially of alkyl alcohol, alkyl acetate, the alkyl group containing from one carbon to five carbons, acetone, methyl ethyl ketone, and any organic solvent.

The hereinafter set forth method contemplates the usage of a woven fiberglass fabric 26 pre-impregnated with, as above noted, a preparation of cellulose, nylon fiber, resin, a plasticizer, and a solvent in which, upon evaporation of the solvent, the preparation forms into a hardened matrix within the weave of the fiberglass fabric.

In a preferred embodiment, the fiberglass fabric weighs in the neighborhood of 45 grams per square meter (this converting into 1.5 ounces per square yard in the English system). Such fiberglass fabric is sold by many vendors, including, for example, S.I.G. Manufacturing Company, Inc., Montezuma, Iowa 50171.

With reference to the figures, FIG. 1 shows the nail 20 prior to treatment. In FIGS. 2 and 3 is shown the optional step of the application of a so-called nail tip 22 to the natural nail, prior to commencement of the present inventive method. The application of nail tips (a plastic material) has long been known and has constituted the first step in every known nail extension method where greater length of the nail is an objective of the customer. The nail tip is nothing more than a plastic substrate or palate which forms the basis for all subsequent steps, whether in this or in any other nail extension methods. As noted, the use of tips is optional and is necessary only where extension, as opposed to reinforcement or strengthening only, is desired. As noted in FIG. 2, the nail tip is first applied, by an adhesive such as cyanoacrylate, to the natural nail. Thereafter, as shown in FIG. 3, the tip is shaped to approximate the configuration and length desired by the customer.

The present method of fingernail extension and reinforcement begins with FIG. 4 in which is shown, in both the longitudinal and transverse axes, the application of a coat of slow-drying cyanoacrylate adhesivve 24 to a portion of the natural nail surface. In this context, the term "slow-drying" means taking from 10 to 20 seconds to dry.

After the slow-drying adhesive has been applied, the adhesive 24 is molded, preferably through the use of a small flat implement 27, into the form of the desired shape of the artificial nail surface. Please note that where tips are used, the slow-drying adhesive 24 is placed over the top of the tip.

In FIG. 5 is shown the application of a wetting agent 25, i.e., a solvent, to the pre-impregnated fabric 26 to provide flexibility thereto prior to its application and usage in the present inventive method.

In FIG. 6A is shown the pressing of the wetted fabric into the molded adhesive, said fabric extending beyond the extent of the natural fingernail. As noted in FIG. 6A, a small brush containing the wetting agents 25 can be used to help in the application of the wetted fabric 26 to the surface defined by the molding step.

In addition, in the step shown in FIG. 6B, the tip of the wetted fabric may be tugged by the technician in order to effectuate the final contour thereof.

In FIG. 7 is shown the trimming of excess fabric on the side of the natural and/or tip to achieve an aesthetic blending therebetween.

In FIG. 8 is shown the step of firmly pressing a coat of fast-drying cyanoacrylate adhesive 28 into the trimmed impregnated fabric. In this context, fast-drying means approximately five seconds.

In FIG. 9 is shown the next step which is that of feather filing the hardened fast-drying adhesive 28 in order to smooth all edges and surfaces thereof.

In FIGS. 10 and 11 are shown the optional step of repeating the steps of FIGS. 8 and 9, as many times as desired, until the desired thickness of the outer artificial nail surface is achieved.

In FIG. 12 is shown the final step of buffing the nail surface to produce the final shape and lustre of the artificial nail. This is the common embodiment, accomplished through the use of cuticle oil to achieve a fine finish of the artificial nail surface.

FIG. 13 is a cross-sectional view of the product resulting from the steps above set forth in which may be seen the artificial nail tip, the fabric, the slow-drying molding adhesive, and the fast-drying finishing adhesive 28.

The fingernail reinforcement and extension method must be resealed at two week intervals. For resealing, feather file each nail, filing any loose edges, and shortening or reshaping the length. Leave residual dust on the filed nail; apply hardening adhesive 28; repeat process on the second coat and buff to smoothness using cuticle oil.

The reinforced nail extension can be permitted to grow off the fingernail if continually resealed until all fiberglass fabric 26 has grown off the nail tip.

The fabric can be removed from the fingernail with any commercial glue remover or oily nail polish remover with baby oil.

The new and improved invention includes the following:

Pre-impregnation of fiberglass cloth with bonding agent; the impregnation of fiberglass cloths with a bonding agent to encase the circumference of the threads in fiberglass without closing the weave of the cloth.

Primary significance-To prevent glass particles from escaping the fiberglass when sanded or filed after glues or resin have been applied.

To prevent shredding and instability of glass cloth when glues or resin applied.

The bonding agent or formula stabilizes the fiberglass cloth creating a firmer cloth, yet, retains the flexibility which allows fiberglass cloths to be used in any manner fiberglass would normally be used.

Impregnated fiberglass, being stabilizwed can now be cut into any shape or design desired, including a bias cut which enables fiberglass to be molded or contoured with simplicity unavailable before processing.

Secondary significance-The stabilized glass cloth prevents glass particals from escaping cloth creating a safer method of working with fiberglass. Unprocessed fiberglass exposed the skin, hair, eyes, clothing can cause extreme itching and irritation when used in normal manner in application of glues or resins and particularly when sanding to smooth finish.

The impregnated fiberglass cloth, can also become self adhesive, when coated with a pressure-sensitive adhesive on one side of the treated glass cloth and pressed onto a release paper backing. Many adhesives and release papers are available, 3M Super 77 and a poly coated release paper is preferred.

The bonding formula to impregnate and encase the fiberglass cloth threads should be determined, as to the use of fiberglass cloth, consideration, commercial or cosmetic. Primary significance is that the chemicals of the bonding formula and glues or resins are compatible for maximum strength and durability.

The present invention pertains to a fingernail reinforcement and extension material comprising a specific fiberglass fabric having a vertical and horizontal cross-thread count in the range of 25–55 threads per inch, and the fabric is preimpregnated with a preparation of cellulose, nylon fiber, resin, plasticizer and solvent. The final product is a hardened matrix within the weave of the fiberglass fabric.

The fingernail reinforcement material in accordance with the claimed invention is a fiberglass fabric preimpregnated with a preparation of a particular composition, not an adhesive; said impregnation is carried out prior to application to the nail. Furthermore, the preparation forms into a hardened matrix within the weave of the fiberglass fabric. None of these features were taught by Umstattd or Litt. The cited references either singly or in combination do not suggest the features as claimed. Therefore, these references do not apply.

The claims are to a material and method involving the pre-impregnation of a fiberglass fabric. The claims to invention include the term fabric and cross-thread count of the fabric and the chemistry of the material with which the woven fabric is pre-impregnated.

While there have been shown and described the preferred embodiments of the present invention, it will be understood that the invention may be embodied otherwise than is herein specifically illustrated or described and that within said embodiments certain changes in the detail and construction, and the form of arrangement of the steps, and the ingredients of the impregnated preparation, may be made without departing from the underlying idea or principles of this invention within the scope of the appended claims.

I claim is:

1. A nail covering for reinforcing a fingernail comprising:
   a woven fiberglass fabric having a vertical and horizontal cross-thread count in the range from 25 to 55 threads per inch, said fabric preimpregnated with a suspension of resin polymer and monomer in water and then allowed to dry, said dried fabric having open interstices between the fabric threads;
   a layer of pressure sensitive adhesive coated on one side of said fabric; and
   adhesion release means adhered to said pressure sensitive adhesive coating.

2. The nail covering as recited in claim 1 in which said resin polymer and monomer comprise acrylic polymer and acrylic monomer.

3. The nail covering as recited in claim 1 is extending along the longitudinal axis of the fingernail, wherein the threads of the fabric are disposed at substantially a 45° angle with respect to the longitudinal axis of the fingernail.

4. The nail covering as recited in claim 3 wherein the resin polymer and monomer suspension is diluted 8 to 16 fold by volume with water.

5. A method for producing a nail covering, comprising:
   (a) spraying a fiberglass fabric, having a vertical and horizontal cross-thread count in the range of from 25 to 55 threads per inch, with a suspension of resin polymer and monomer in water to mechanically stabilize said fabric;
   (b) allowing the fabric to dry to permit the interspace between the fabric threads to remain open;
   (c) coating one side of the fabric with a pressure sensitive adhesive; and
   (d) pressing the adhesive-coated side of the fabric onto an adhesion release means.

6. The method according to claim 5 in which said adhesion release means is rectangular, and the threads of said fabric are disposed at a 45° angle with respect to the sides of said release means.

7. The method according to claim 6 wherein the resin polymer and monomer are acrylic polymer and acrylic monomer.

8. The method according to claim 6 wherein the resin polymer and monomer suspension is diluted 8 to 16 fold by volume with water.

9. The method according to claim 6 wherein the pressure sensitive adhesive defines a self-adhesive backing on the nail covering.

10. A method of reinforcing nails, comprising:
    (a) peeling a precut strip of a nail covering from an adhesion release means, said nail covering comprising:
        (i) a woven fiberglass fabric having a vertical and horizontal cross-thread count in the range from 25 to 55 threads per inch, said fabric preimpregnated with a suspension of resin polymer and monomer in water and then allowed to dry, said dried fabric having open interstices between the fabric threads;
        (ii) a layer of pressure sensitive adhesive coated on one side of said fabric; and adhesion release means adhered to said pressure sensitive adhesive coating;
    (b) pressing and aligning said existing nail covering onto the fingernail;
    (c) trimming off excess nail covering;
    (d) coating the nail covering with adhesive; and
    (e) allowing the adhesive to penetrate the interstices between the threads of the nail covering and to contact the fingernail surface, whereby a firm bond between the nail covering and the fingernail is formed when the adhesive is dried.

11. A fingernail reinforcement and extension material, comprising:
    (a) a woven fiberglass fabric having a vertical and horizontal cross-thread count in the range of 25 to 55 threads per inch; and
    (b) a preparation impregnated within the weave of said fabric, said preparation consisting essentially of cellulose, nylon fiber, resin, plasticizer and solvent, whereby upon evaporation of said solvent, said preparation forms a hardened matrix within the weave of said fiberglass fabric.

12. The material as recited in claim 11 in which said cellulose is selected from the group consisting of nitrocellulose and cellulose acetate.

13. The material as recited in claim 11 in which said resin comprises a synthetic resin.

14. The material as recited in claim 13 in which said synthetic resin comprises toluene sulfonamideformaldehyde.

15. The material as recited in claim 11 in which said plasticizer is selected from the group consisting of di-alkyl phthalates, alkyl stearates, camphor, castor oil, coconut oil and any combination thereof.

16. The material as recited in claim 15 in which said di-alkyl phthalates comprise dibutyl and diethyl phthalates.

17. The material as recited in claim 11 in which said solvent is an organic solvent.

18. The material as recited in claim 11 further comprising:

(a) a solvated wetting agent employed to soften the hardened fiberglass fabric for purposes of application thereof to a natural nail surface.

19. The material as recited in claim 18 in which said wetting solution solvent is an organic solvent.

20. A method of reinforcing and extending a natural fingernail, comprising the steps of:
    (a) pre-impregnating a woven fiberglas fabric with a preparation consisting essentially of cellulose, nylon fiber, resin, plasticizer and solvent, wherein upon evaporation of said solvent, said preparation forms a hardened matrix within the weave of said fiberglass fabric thus defining an artificial fingernail;
    (b) applying a coat of slow-drying cyanoacrylate adhesive to a portion of the natural fingernail surface;
    (c) molding said adhesive into the form of the desired shape of the artificial fingernail surface;
    (d) applying a wetting agent into said impregnated fabric to provide flexibility thereto;
    (e) applying a piece of said wetted impregnated fabric over said molded adhesive, said fabric extending beyond the extent of the natural fingernail;
    (f) pressing said fabric firmly into said molded adhesive, thereby eliminating air bubbles therefrom and contouring said fabric into the desired shape for the artificial fingernail surface;
    (g) tugging the tip of the impregnated fabric to effectuate final contour therof;
    (h) trimming excess fabric on the sides of said natural fingernail to achieve blending therebetween;
    (i) pressing a coat of fast-drying cyanoacrylate adhesive into said impregnated fabric;
    (j) feather filing the hardened adhesive to smooth all edges thereof;
    (k) repeating Steps (i) and (j) until the desired thickness of the artificial fingernail is achieved; and
    (l) buffing the hardened fast-drying adhesive to produce the final shape and lustre of the artificial fingernail.

21. A method of reinforcing and extending a natural fingernail using a woven fiberglass fabric impregnated with a preparation consisting essentially of cellulose, nylon fiber, resin, plasticizer and solvent, in which, upon evaporation of said solvent, said preparation forms a hardened matrix within the weave of the fiberglass fabric thus defining an artificial fingernail, the inventive method comprising the steps of:
    (a) applying a coat of slow-drying cyanoacrylate adhesive to a portion of the natural fingernail surface;
    (b) molding said adhesive into the form of the desired shape of the artificial fingernail surface;
    (c) applying a wetting agent into said impregnated fabric to provided flexibility thereto;
    (d) applying a piece of said wetted impregnated fabric over said molded adhesive, said fabric extending beyond the extent of the natural fingernail;
    (e) pressing said fabric firmly into said molded adhesive, thereby eliminating air bubbles therefrom and contouring said fabric into the desired shape for the artificial fingernail surface;
    (f) trimming excess fabric on the sides of said natural fingernail to achieve blending between said fabric and the natural fingernail;
    (g) pressing a coat of fast-drying cyanoacrylate adhesive into said impregnated fabric; and
    (h) feather filing the hardened adhesive to smooth all edges and surfaces thereof.

22. The method as recited in claim 21, further comprising the steps of: applying said fast-drying adhesive and of feather filing said hardened adhesive, continuing such repetition until the desired thickness of the artificial nail is achieved.

23. The method as recited in claim 22 further comprising, between said pressing and said trimming steps, the step of: tugging the tip of the impregnated fabric to effectuate the final contour thereof.

24. A method of reinforcing and extending a natural fingernail comprising the steps of:
    (a) applying a coat of slow drying cyanoacrylate adhesive to a portion of the natural fingernail surface;
    (b) molding said adhesive into the form of the desired shape of an artificial fingernail surface;
    (c) applying a wetting agent to a preimpregnated fiber-glass fabric which had previously been hardened with the impregnating preparation comprising cellulose, nylon fiber, resin, plasticizer and solvent;
    (d) applying fabric of step (c) over said molded adhesive, said fabric extending beyond the extent of the natural fingernail;
    (e) pressing said fabric firmly into said molded adhesive and contouring said fabric into the desired shape of the artificial fingernail;
    (f) trimming excess fabric to conform to the natural fingernail;
    (g) applying a coat of fast-drying adhesive to smooth all edges thereof; and
    (h) feather-filing and buffing the hardened adhesive to final shape and lustre.

25. The method as recited in claim 24 further comprising, as the very first step thereof, the step of:
    applying a pre-formed artificial fingernail substrate directly upon the natural fingernail surface, prior to said step of applying a coat of slow-drying cyanoacrylate adhesive.

* * * * *